United States Patent [19]

Lovegrove

[11] 4,286,588
[45] Sep. 1, 1981

[54] MEDICAL SUPPORT BOARD

[76] Inventor: Paul D. Lovegrove, 2573 Merrywood Ct., Woodbridge, Va. 22192

[21] Appl. No.: 58,416

[22] Filed: Jul. 18, 1979

[51] Int. Cl.$^3$ .............................................. A61F 13/00
[52] U.S. Cl. ............................ 128/133; 128/DIG. 6; 128/DIG. 15
[58] Field of Search ................. 128/214, DIG. 6, 133, 128/DIG. 15, 87 R, 94

[56] References Cited

U.S. PATENT DOCUMENTS

| | | | |
|---|---|---|---|
| 2,693,794 | 11/1954 | Neville | 128/DIG. 6 |
| 3,469,268 | 9/1969 | Phillips | 128/87 R |
| 3,724,456 | 4/1973 | Waxman | 128/DIG. 6 |
| 3,812,851 | 5/1974 | Rodriguez | 128/133 |
| 3,815,588 | 6/1974 | Klausner | 128/94 |

Primary Examiner—John D. Yasko
Attorney, Agent, or Firm—Howard L. Bernstein

[57] ABSTRACT

A medical support board to inhibit movement of a patient's limb is provided. The support board is provided with an adherent strip applied to its reverse side. The adherent strip is a removably adherable to materials underlying the support board such as carpets, blankets or the clothing of the patient. The adherent strip adherring to an underlying material inhibits movement of the patient's limb relative to the body. Straps are provided to secure the limb to the support board and are fastened by means of adherent strips.

6 Claims, 7 Drawing Figures

MEDICAL SUPPORT BOARD

BACKGROUND OF THE INVENTION

This invention relates generally to a means for supporting a limb of a person receiving medical treatment. More particularly, the present invention provides a medical support board that inhibits movement of a patient's limb. Two specific applications of the medical support board, and not limiting ones, is as a support to inhibit movement of a patient's limb while receiving an intravenous medicament or during defibrillation. A general application, and again not a limiting one, is for emergency situations wherein the medical support board can be rapidly attached and detached and is removably adherable to materials underlying the support board to inhibit movement of the patient's limb. The underlying materials may be carpets, blankets, the patient's clothing or the like.

In emergency situations, such as those that face emergency personnel, for example, members of a rescue squad, there is a need for a medical support board that is convenient for use in a variety of circumstances. The variety of circumstances that can face emergency personnel are too numerous to list or even imagine but the following are illustrative:

a. A patient requiring an intravenous medicament thus requiring the elbow joint, forearm and/or wrist and hand being rigidly supported;
b. A patient requiring transportation to a medical facility and requiring the limb to be stabilized relative to the body;
c. A multiple injury incident wherein a plurality of injured persons require rapid and effective treatment; and
d. A situation wherein a person may be unconscious, disorderly or violent, uncooperative, or requires cardioversion or defibrillation during cardiac arrest.

These circumstances are but a few of the variety that can face emergency personnel; however, it can be seen from these few circumstances that the following are minimum requirements for the medical support board:

a. Because of the limited storage space on typical rescue vehicles there is a requirement for a multi-purpose device that can be used for as many situations as possible and can be disassembled for storage in as limited a space as possible;
b. Because of the emergency situation the device must be capable of being attached and detached rapidly and effectively;
c. Because of the possibility of having to treat more than one person it is necessary that the device be effectively attached and remain attached securely while the attendant is attending another person;
d. Because of the necessity of transporting a patient to a hospital or other facility the device must be capable of being secured so that the limb will be stabilized relative to the body;
e. Because there are situations wherein the patient is violent, disorderly or needs defibrillation the device needs to be capable of being rapidly and securely attached to a stationary surface to prevent the arm from moving and dislodging the I.V. or to further prevent aggravation of an injury.
f. Because there are situations wherein an injury may require a plurality of straps placed in a variety of locations on the limb the device must be capable of having a plurality of straps attachable anywhere on the device.

The prior art discloses boards and strap assemblies in various configurations, however, none of them meet the minimum requirements for those devices.

SUMMARY OF THE INVENTION

The present invention overcomes the disadvantages of prior support boards by providing a medical support board and strap assembly that can be rapidly attached and detached, is easily disassembled for storage in a small area and is further attachable to underlying material to inhibit movement of the limb relative to the body. There is provided a rigid support board and a plurality of straps to tightly encircle the limb and the support board. The support board is padded on the side that is disposed next to the limb while the opposite side is provided with a strip of adherent or adhesive material which may extend along the length of the board. The straps are of a sufficient length to encircle and overlap and injured person's limb and the support board. The straps are constructed with adherent material placed on both sides of the strap so that when overlapped the overlapped sections adhere to each other.

Accordingly, an object of the present invention is the provision of a medical support board that is adherable to a material underlying the board to inhibit movement of the board and limb relative to the body of the patient.

Another object of the present invention is the provision of a medical support board and strap assembly that can be rapidly attached and detached to and from the material underlying the board and from the patient's limb.

A further object of the present invention is the provision of a medical support board and strap assembly having a plurality of straps removably attachable to the support board at any position on the board and is thus adaptable for a variety of uses.

Still another object of the present invention is the provision of a medical support board and strap assembly that is simple and thus inexpensive and which is easily disassembled for compact storage.

Other objects, advantages and novel features of the present invention will become apparent from the following detailed description of the invention in conjunction with the accompanying drawings.

DESCRIPTION OF THE PREFERRED EMBODIMENT

Figure 1:
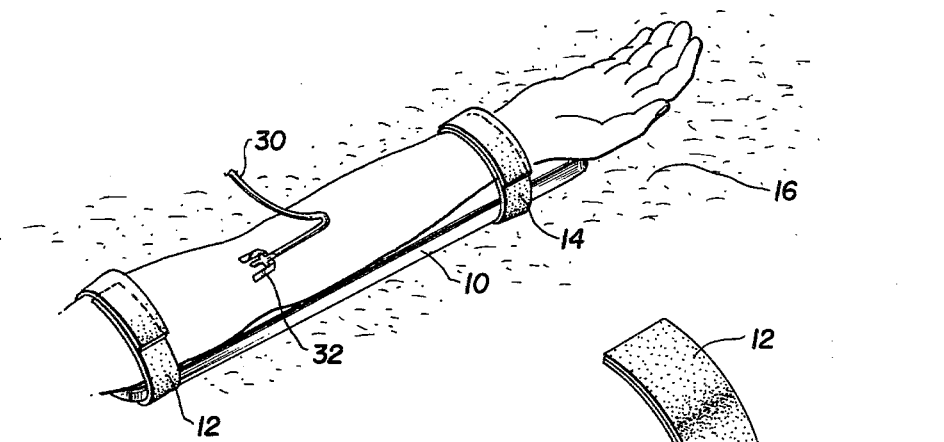
FIG. 1 is a pictorial view of the present invention securing a persons arm to the board and the board adhering to an underlying material.

The medical support board and strap assembly of the present invention will now be described in connection with FIGS. 1 through 6. FIG. 1 is a pictorial view of the present invention with a person's arm supported thereon. The arm is held on the support board 10 by straps 12 and 14. It is noted that while the description hereinafter discusses the use of the present invention in relation to an arm however, legs are also applicable. It is also noted that throughout this description only two straps will be shown, however, it is understood that more than two straps can be used and may be necessary in certain situations. FIGS. 1 and 4 show the concept of the support board adhering to a cloth or fabric material 16 underlying the board, which may be a carpet, a blanket, clothing of the patient, etc., these materials being susceptible of adhering to the adhering material 18 employed in the present invention. Any adherent material may be used, however, the preferable type of adherent material is materially commonly known as hook material. Hook material, which is manufactured by several manufacturers, is sometimes known as Velcro material, after the name of one of its manufacturers, Velcro Manufacturing Co. This material is known and described, for example, in U.S. Pat. No. 3,640,273, which issued Feb. 8, 1972 to Tommy D. Ray. Strip 18 on the bottom side 20 of board 10 is the monofilament type hooks of the "Velcro" fastener. These monofilament type hooks adhere to cloth or fabric materials such as carpets, blankets, clothing, etc., that in most instances are disposed beneath or on a patient.

Figure 5:
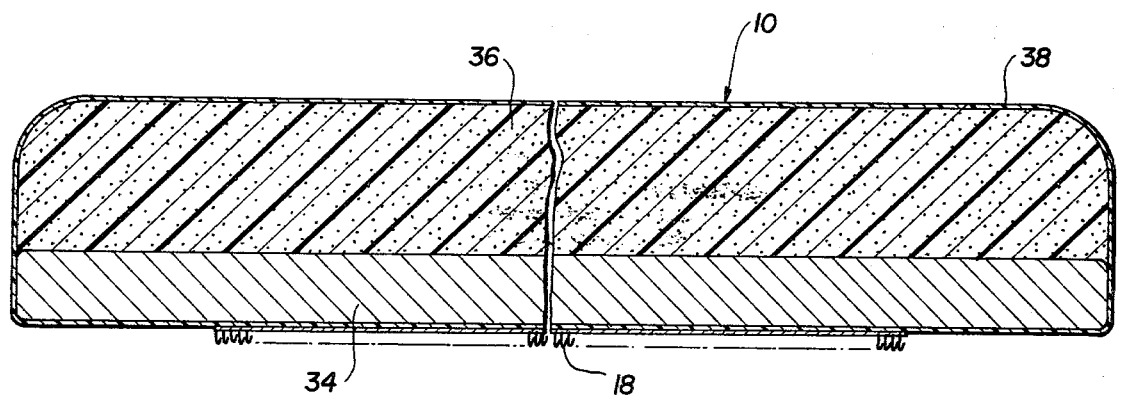
FIG. 5 is a cross sectional view of the support board.

The straps 12 and 14 are made of any strong flexible material, such as a woven synthetic type material such as that used for seatbelts. The straps 12 and 14 are also provided with a "Velcro" fastener. The outwardly facing sides 22 and 24 of the straps 12 and 14 are provided with the monofilament hooks of the "Velcro" fastener. The inwardly facing sides 26 and 28 of the straps 12 and 14 are provided with the "Velcro" type pad. The inwardly facing sides 26 and 28 may have the "Velcro" type pad attached the entire length of straps 12 and 14 or any intermediate length. A preferable embodiment is shown in FIG. 5 wherein the adherent material does not extend the length of the straps 12 and 14. A space 27 is provided, free of adherent material to allow the board 10 to be easily adjustable on the patient's limb. The principal purpose of the inwardly facing strips 26 and 28 is to provide an adherent "Velcro" type pad to adhere to the monofilament "Velcro" type hooks disposed on the overlapping outwardly facing sides 22 and 24 of straps 12 and 14 respectively. As can be seen from FIG. 2, the outwardly facing sides 22 and 24 being provided with the monofilament "Velcro" type hooks add to the adhering strength of the adhering strip 18 disposed on board 10 by providing additional area of monofilament "Velcro" type hooks that are adherable to an underlying material 17.

Figure 3:
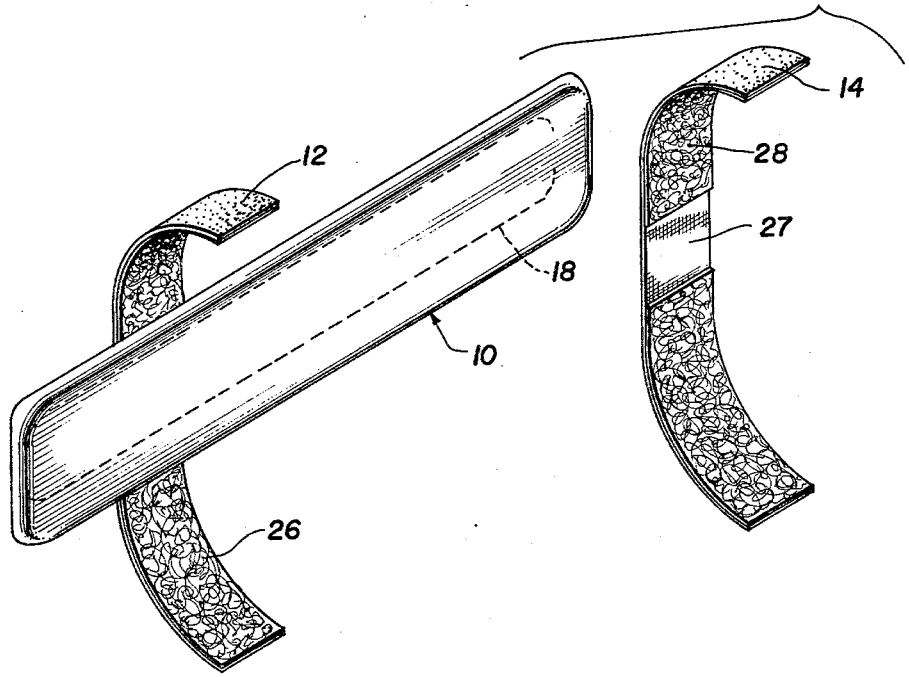
FIG. 3 is a top view of the support board showing the board and two straps, one of which is unattached from the board.
Figure 4:
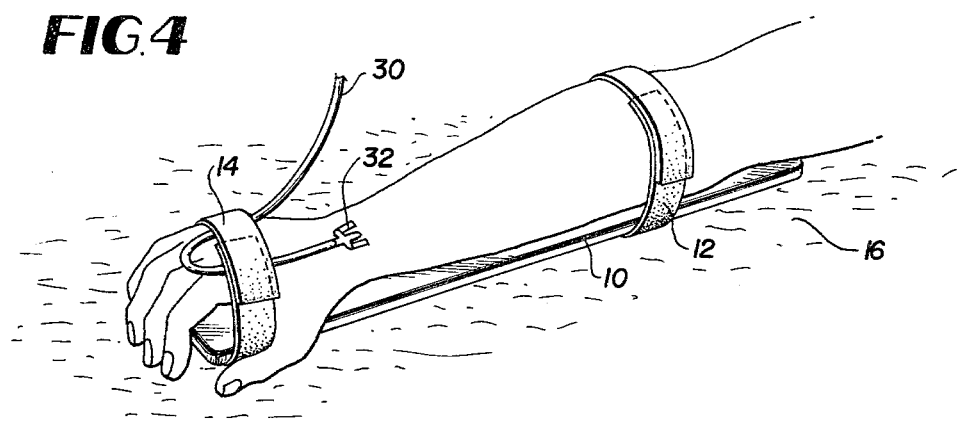
FIG. 4 is a pictorial view of an alternate use of the present invention.

FIG. 3 shows the concept of the easy removal of the straps 12 and 14. The straps being easily detached and attached can be disposed at any position on the board 10 and any number of straps may be disposed, limited of course to the available area provided by the length of the board 10 and the width of the straps.

Figure 2:
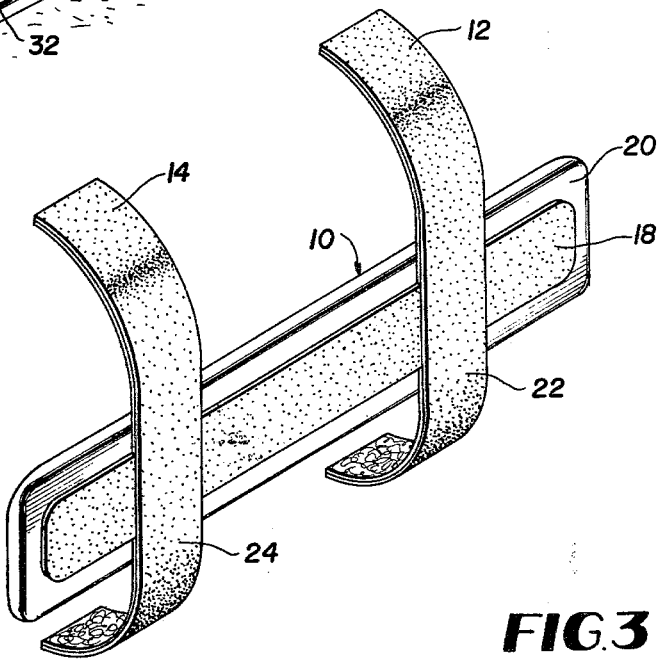
FIG. 2 is a bottom view of the support board showing two straps in an open position.

FIG. 4 shows the medical support board being used as an arm restraint for the application of an intravenous medicament. The board 10 is shown with an underlying material 16 to which the adherent strip 18 FIG. 2 is adhered. As can be seen from FIGS. 2, 3 and 4 and a consideration of an emergency situation, such as a heart attack where time is of the essence, the board 10 has major advantages and is used as follows: The board 10 with straps attached as in FIG. 2 can be placed upon a surface 16 to which it will adhere and the patient's arm placed thereon and the straps 12 and 14 rapidly secured. The I.V. 30 is then administered and taped by a strip of tape 32, all within a matter of seconds. The attendant can then move on to further treatment procedures, for example, defibrillation. The application of the high voltage pulse in defibrillation procedures causes the limbs of even an unconscious patient to spasm violently. Because of the high voltage, the attendants do not hold the limbs of the person being difibrillated and this causes a danger of the I.V. being pulled out or the I.V. needle or catheter being broken off or crimped in the person's vein. By catheter is meant a flexible hollow tube usually of a plastic material in which is inserted into the patient by means of a pointed steel shank initially inserted into the tube hollow. The steel shank is thereafter withdrawn from the patient through the tube, leaving the tube, unsupported in the patient. Since the tube is flexible it is subject to crimping to which will ceast the flow of fluid. The strip 18 disposed on the underside 20 of board 10 prevents the arm being moved, either involuntarily or voluntarily by the patient. At the same time, however, the attendant can free the board 10 from the underlying material 16 rapidly by an upward motion so the patient can be transported. During transportation, the board 10 can be adhered to another material such as a blanket underlying the patient and the board or it may be adhered to the patient's clothing.

FIG. 5 shows a cross-sectional view of the preferable embodiment of the support board. The board 10 consists of a rigid member 34 with a section of padding 38 to cushion the limb with a washable plastic covering 38 surrounding the member 34 and padding 36. The adherent strip 18 is permanently attached to the underside of board 10.

Figure 6:
FIG. 6 shows the present invention disassembled and connected together for storage.

FIG. 6 shows the board 10 and straps 12 and 14 disassembled and placed in a storage condition. The adherent strips disposed on either side of the straps 12 and 14 allow the placing together of the board 10 and strips 12 and 14 for easy and compact storage. Furthermore, the monofilament "Velcro" type hooks extending from strap 14 in FIG. 6 allows the board to be stored in an easily accessible position within the rescue vehicle. For example, a strip of adherent material placed in a convenient location would hold the board 10 and straps 12 and 14 securely.

Figure 7:
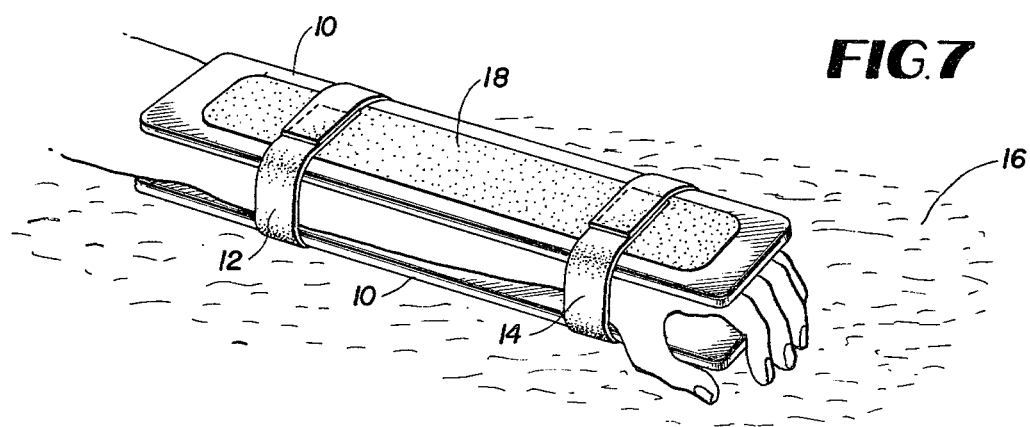
FIG. 7 shows two boards constructed according to the present invention used as a splint.

FIG. 7 illustrates the use of the support boards of the present invention as a limb splint. In the FIG. 7 embodiment, two support boards such as illustrated in FIGS. 2 and 3 herein are used with a single pan of straps 12, 14 to support a broken limb. The adherent strip on the underside of the boards function as previously described.

Thus, a new and novel medical support board is provided that is rapidly attachable and detachable is adaptable for a variety of uses and is attachable to a material underlying the injured person.

Although the invention has been described and illustrated in detail, it is to be clearly understood that the same is by way of illustration and example only and is not to be taken by way of limitation, the spirit and scope of the invention being limited only to the terms of the appended claims.

What is claimed:

1. An IV support board particularly adapted for emergency use comprising a rigid support member, padding covering one side of said rigid support member and adherent material for removably adhering to a cloth or fabric material underlying said rigid support member, said adherent material covering substantially the entire area of the side of the support member opposite the padded side whereby movement of said support board is inhibited by the adherence of the board to the underlying cloth or fabric material.

2. An IV support board as claimed in claim 1, further including a washable cover surrounding said rigid support member and said padding but not said adherent material.

3. An IV support board as claimed in claim 2, wherein said adherent material is hook material having rows of hook-like appendages.

4. An IV support board as claimed in claim 3, wherein said adherent material is Velcro material.

5. A medical support board comprising:
a. means for providing rigid support to a patient's limb; and
b. a strip of hook material attached to and covering substantially the entire side of said rigid support means disposed away from said limb for removably adhering said rigid support means to a cloth or fabric material underlying said rigid support means to substantially inhibit uncontrolled limb movement as is likely to occur during defibrillation or movement of a paralyzed or unconscious patient.

6. A medical support board comprising:
a. means for providing rigid support to a patient's limb; and
b. a strip of Velcro material attached to and covering substantially the entire side of said rigid support means disposed away from said limb for removably adhering said rigid support means to a cloth or fabric material underlying said rigid support means to substantially inhibit uncontrolled limb movement as is likely to occur during defibrillation or movement of a paralyzed or unconscious patient.

* * * * *